United States Patent [19]

Merry

[11] Patent Number: 4,519,800

[45] Date of Patent: May 28, 1985

[54] DIAPER AND METHOD OF MAKING THE SAME

[76] Inventor: Terri J. Merry, R.F.D. #1, Box 1780, Anson, Me. 04911

[21] Appl. No.: 425,272

[22] Filed: Sep. 28, 1982

[51] Int. Cl.³ .............................................. A61F 13/16
[52] U.S. Cl. ................................................ 604/385 A
[58] Field of Search ............... 604/385, 386, 358, 393, 604/394, 387

[56] References Cited

U.S. PATENT DOCUMENTS 2,852,026  9/1958  Karr ................................. 604/385 X
3,559,648  2/1971  Mason, Jr. ........................... 604/387
4,410,324  10/1983  Sabee ............................... 604/385 X Primary Examiner—John D. Yasko

[57] ABSTRACT

A reuseable diaper is formed from a length of absorbent fabric by cutting a central portion of each side thereof to form flaps which are folded over the middle section and are stitched thereto thus providing a crotch portion of increased moisture absorbing capacity and leg recesses. Elastic lengths are incorporated in each margin of the crotch portion of the diaper.

5 Claims, 5 Drawing Figures

FIG. 3
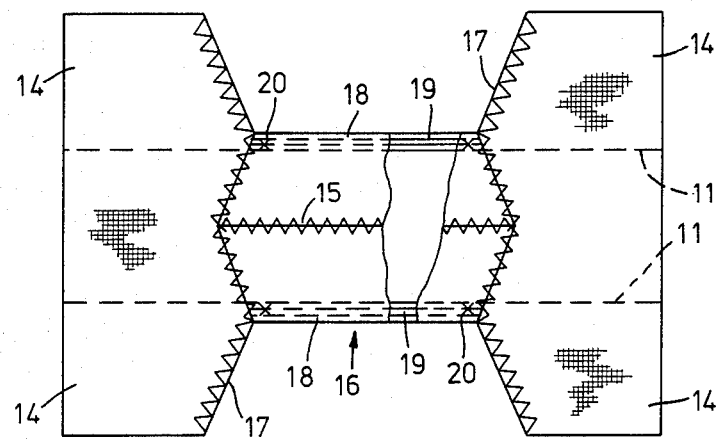
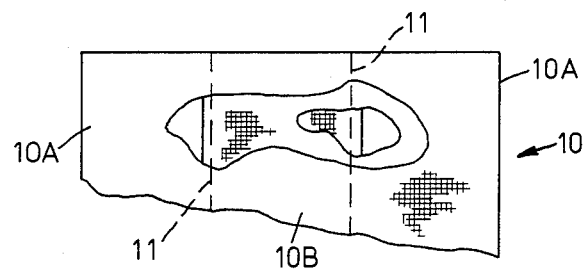
FIG. 5
FIG. 4
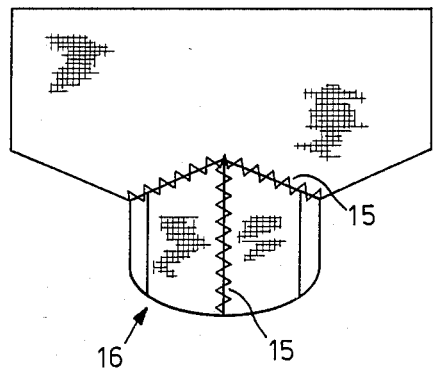

DIAPER AND METHOD OF MAKING THE SAME

BACKGROUND REFERENCES

U.S. Pat. No. 1,694,161
U.S. Pat. No. 3,848,595
U.S. Pat. No. 3,860,003
U.S. Pat. No. 3,860,004
U.S. Pat. No. 3,920,017

BACKGROUND OF THE INVENTION

Disposable diapers, while expensive in comparison with reuseable diapers, are widely used both because of the convenience they afford and because of the ease of putting them on a baby and the good fit then resulting, particularly in the case of the type having elasticized leg recesses.

THE PRESENT INVENTION

The general objective of the present invention is to provide reuseable diapers that are as easy to put on and be well fitted to a baby as disposable diapers and have increased moisture absorbing capacity as compared with conventional reuseable diapers.

In accordance with the invention, this objective is attained, in terms of method by selecting a length of absorbent fabric of appropriate width, severing the sides centrally thereof to provide flaps, folding the flaps over the central or crotch portion of the middle section, stitching the flaps thereto to establish leg recesses and to increase the moisture absorbing capacity of the crotch portion, and, in preferred embodiments, incorporating elastic material in the margins of the crotch portion.

The material may be prefold diapers of lengths cut from absorbent fabric folded and stitched lengthwise to be of the appropriate width with marginal sections of double thickness and a central section of triple thickness.

Another objective of the invention is to ensure that the length of the crotch portion, where the moisture absorbing capacity is increased, is adequate and the end portions of tabs of the side sections are dimensioned for conveniently joining them about the legs and body of a baby. This objective is attained by cutting the side sections along lines extending inwardly towards each other whereby the flaps extend lengthwise of the crotch portion to the wanted extent beyond the ends of the side margins thereof.

In terms of the articles, diapers in accordance with the invention are of absorbent fabric, conveniently prefolded reuseable diaper material, having leg recesses centrally of its side sections with the crotch portion having flaps secured thereto, the flaps resulting from the forming of the leg recesses and secured to the crotch portion to increase the moisture absorbing capacity thereof. In preferred embodiments, the margins of the crotch portion have elastic material incorporated therein to yieldably shorten them.

In preferred embodiments, the flaps taper inwardly, preferably with both edges thereof extending inwardly towards each other, so that the length of the crotch portion where its moisture content is increased, is greater than the length of its margins whether or not the margins are elasticized.

PRIOR ART STATEMENT

In addition to the disposable diapers to which previous reference has been made, the previously cited patents are examples of disposable diapers shaped to provide a good fit. These are not pertinent to the present invention as none even suggest the claimed features thereof.

BRIEF DESCRIPTION OF THE DRAWINGS

The accompanying drawings illustrate a preferred embodiment of the invention

FIG. 3 is another like view but of the diaper finished, the elastic margins of the crotch portion still stretched;

FIG. 4 is a view of the diaper folded in half and with the elastics released to shorten the crotch margins; and FIG. 5 is a fragmentary and partly sectioned plan view of the material.

THE PREFERRED EMBODIMENT OF THE INVENTION

Figure 1:
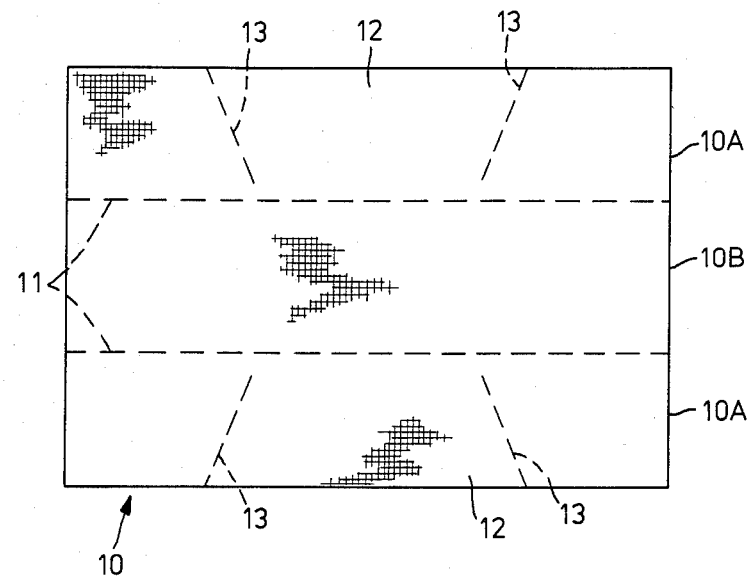
FIG. 1 is a somewhat schematic plan view of a suitable length of absorbent fabric with flap forming lines of severance indicated.
Figure 2:
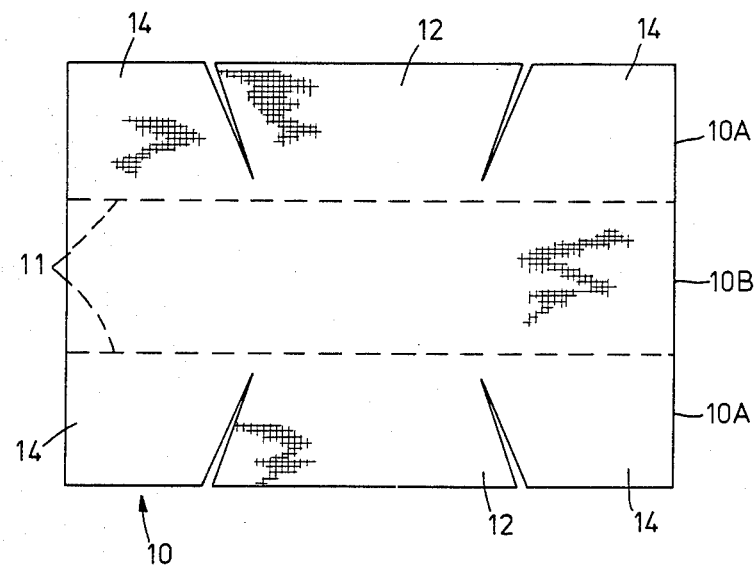
FIG. 2 is a like view but with the flaps formed.

A diaper is formed from a blank 10 of absorbent material of a wanted length and width and is shown, see FIG. 5, as prefolded and stiched along lines 11 to establish side sections 10A of double thickness and a central section 10B of triple thickness. By way of example and not of limitation, the width of the blank is twelve inches and its length sixteen inches. The width of the section 10B is greater than that of the sections 10A, five inches for the former and three and one-half inches for the latter.

The central portion 12 of each side section 10A is severed along lines 13 which extend inwardly towards each other to form a flap with the lines of severance terminating close to but short of the proximate line of stitching 11. It has been found that flaps 12 and end portions or tabs 14 result, again by way of example and not of limitation, with the outer end of each line 11 three and one-half inches from the proximate end of the blank 10 and its inner end five inches therefrom.

The flaps 12 are folded over the central portion of the section 10B and their slightly overlapping margins then connected thereto by central and end lines of stitching 15, shown as of the zig-zag type. The thus established crotch portion, generally indicated at 16, has increased moisture absorbing capacity due to the added fabric layers and of greater length than the margins thereof.

Like stitching 17 joins the folded over proximate margins of the end tabs 14. It should be noted that if the blanks 10 are completed prefolded diapers, the other margins of the blanks will have been previously finished to prevent ravelling.

The diaper is completed by a line of stitching adjacent each margin of the crotch portion 16 which provide casings 18 for tensioned lengths 19 of elastic the ends of which are anchored as by stitching 20.

Both the diaper and the method by which it is made is apparent from the foregoing and such a diaper is easy to put on a baby with a proper fit resulting when the tabs 14 are connected about the baby's body by pins or otherwise.

I claim:

1. A reusable diaper, said diaper consisting of a blank of an absorbent fabric of predetermined length and width having central and marginal lengthwise sections, the central portion of the central section, the crotch engaging portion of the diaper, each marginal section divided to provide end portions and a central flap portion, said flap portions folded over the crotch portion and dimensioned and so disposed that they overlap in said crotch portion and are secured thereto by a line of stitching and thereby increase the moisture absorbing capacity of said crotch portion and from a leg recess and end tabs, the end tabs of each marginal section connectable about the body of a baby, and a length of elastic material extending lengthwise of each margin between the crotch portion and the overlapping flap portion with its ends anchored to the central section adjacent the ends of the central portion with the elastic material under tension thereby to yieldably shorten the margins of the central portion.

2. The reuseable diaper of claim 1 in which the fabric length consists of integral lengthwise sections, outer sections of two layers and a central section of three layers.

3. The reuseable diaper of claim 1 in which each overlapping portion is connected by a line of stitching to the crotch portion inwardly thereof and of the elastic material.

4. The method of making a reusable diaper that consists of selecting a substantially rectangular blank of an absorbent fabric of predetermined length and width and having a central portion that is to be the crotch engaging portion, severing both sides of the fabric length to provide end portions and intermediate flap portions dimensioned to overlie the crotch portion and overlap each other, securing together the overlap of said flap portions thereby to increase the moisture absorbing capacity of the crotch portion and establish leg recesses and end tabs, said end tabs dimensioned to be connectable about the body of a baby, positioning a length of elastic material between each margin of the crotch portion and the overlapping flap portion, anchoring the ends of each length to the blank adjacent the ends of the crotch portion under tension to yieldably shorten the margins thereof, and confining each of said lengths of elastic material by a line of stitching spaced inwardly of the appropriate one of said margins and lengths.

5. The method of claim 4 in which the step of securing together the overlap of said flap portion is effected by a line of stitching.

* * * * *